(12) United States Patent
Nicolas et al.

(10) Patent No.: US 8,309,074 B2
(45) Date of Patent: Nov. 13, 2012

(54) **USE OF A FERMENTED MILK CONTAINING *L. CASEI* FOR THE MANUFACTURE OF A COMPOSITION FOR THE PREVENTION OR TREATMENT OF A DELAYED-TYPE HYPERSENSITIVITY REACTION**

(75) Inventors: Jean François Nicolas, Lyons (FR); Catherine Goujon, Lyons (FR); Raphaëlle Bourdet-Sicard, Palaiseau (FR); Nathalie Rolf-Pedersen, Jouy-en-Josas (FR)

(73) Assignee: Compagnie Gervais Danone, Paris (FR)

( * ) Notice: Subject to any disclaimer, the term of this patent is extended or adjusted under 35 U.S.C. 154(b) by 985 days.

(21) Appl. No.: 11/795,849

(22) PCT Filed: Jan. 20, 2006

(86) PCT No.: PCT/EP2006/001430
§ 371 (c)(1),
(2), (4) Date: Nov. 14, 2008

(87) PCT Pub. No.: WO2006/077171
PCT Pub. Date: Jul. 27, 2006

(65) Prior Publication Data
US 2009/0068149 A1    Mar. 12, 2009

(30) Foreign Application Priority Data
Jan. 21, 2005   (EP) ..................................... 05290133

(51) Int. Cl.
*A01N 63/00*   (2006.01)
*A61K 45/00*   (2006.01)
*A61K 39/02*   (2006.01)

(52) U.S. Cl. ................ 424/93.45; 424/282.1; 424/234.1; 514/861

(58) Field of Classification Search ........................ None
See application file for complete search history.

(56) References Cited

U.S. PATENT DOCUMENTS

| 2002/0142005 A1 | 10/2002 | Horn et al. |
| 2004/0029127 A1 | 2/2004  | Postaire et al. |

FOREIGN PATENT DOCUMENTS

| EP | 1 034 788 | 9/2000 |
| WO | WO 02/28402 A1 | 4/2002 |

OTHER PUBLICATIONS

Chapat et al. Eur. J. Immunol. 34: 2520-2528, Sep. 2004.*
Cavani et al. J. Invest. Dermatol. 111: 621-628, 1998.*
Yokoyama. Nature Immunology 7: 437-439, May 2006.*
Oozeer et al. Appl. Environ. Microbiol. 68: 3570-3574, 2002.*

* cited by examiner

*Primary Examiner* — S. Devi
(74) *Attorney, Agent, or Firm* — Morgan, Lewis & Bockius LLP

(57) ABSTRACT

The present invention relates to the field of probiotics. More particularly, the invention pertains to the use of a particular strain, *Lactobacillus casei* CNCM I-1518, which is present in Actimel®, for alleviating the symptoms of a delayed-type hypersensitivity reaction.

7 Claims, 3 Drawing Sheets

Figure 1:
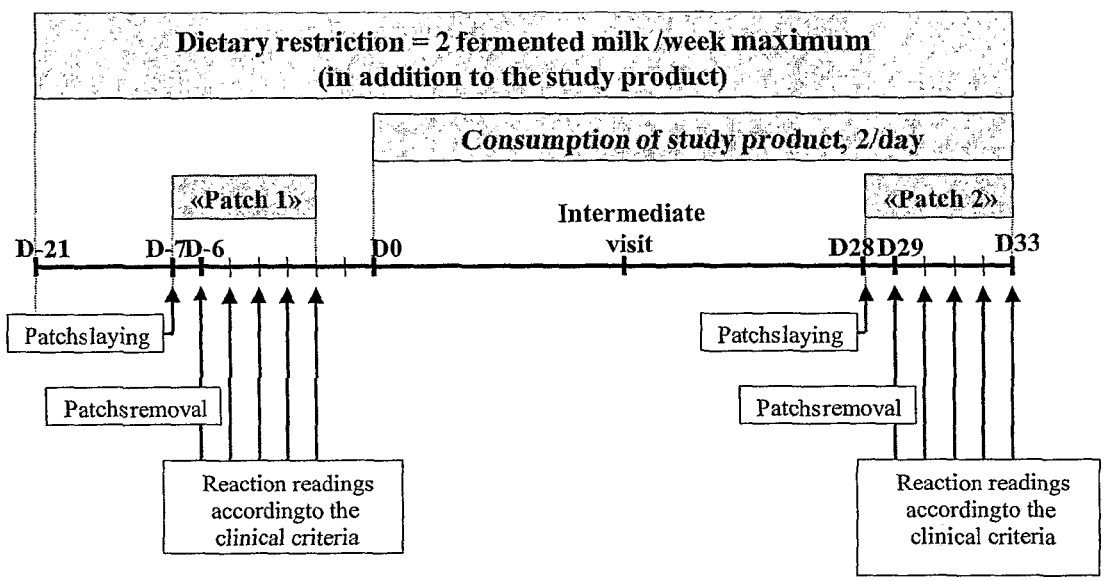

USE OF A FERMENTED MILK CONTAINING L. *CASEI* FOR THE MANUFACTURE OF A COMPOSITION FOR THE PREVENTION OR TREATMENT OF A DELAYED-TYPE HYPERSENSITIVITY REACTION

The present application is a U.S. National Phase Application of International Application No. PCT/EP2006/001430, filed Jan. 20, 2006, which claims the benefit of European Patent Application No. 05290133.7, filed Jan. 21, 2005, both of which are hereby incorporated by reference in their entirety.

The present invention relates to the field of probiotics. More particularly, the invention pertains to the use of a particular strain, *Lactobacillus casei* DN-114 001 (CNCM I-1518), which is present in Actimel®, for delaying the apparition and/or alleviating the symptoms of a delayed-type hypersensitivity reaction. This kind of delayed-type hypersensitivity reaction is responsible for the appearance of symptoms of eczema.

Eczema is the most frequently diagnosed dermatitis: one third of all subjects consulting a hospital dermatological unit are suffering from eczema. There are two main types of eczema:
  Allergic contact dermatitis (Eczema)
  Constitutional eczema, also called atopic dermatitis (which has not been studied herein).

Contact eczema is localised on the skin. It is an allergic reaction caused when the skin comes into contact with a foreign substance called allergen. Contact eczema involves a reaction of hypersensitivity of type IV, with an immune response of cellular type. The inducing allergens are haptens (low molecular weight molecules). They cross the corneum stratum, and come into contact, in the mid-part of the epidermis, with Langerhans cells, which are epidermic dendritic cells, growing from the mesenchymium and having immunological properties. The Langerhans cells transduct the antigenic information to the T lymphocytes, which become specifically sensitised to the antigen and spread into the body. On the occasion of a subsequent contact with the same antigen, the sensitised lymphocytes produce lymphokines, an inductor of the derma-epidermal inflammatory reaction of the eczema (Krasteva, Kehren et al. 1999 a; Krasteva, Kehren et al. 1999 b).

After the first onset, the immune hypersensitivity is generally definitive.

The treatment of contact eczema commonly requires topical administration of corticoids. The best solution if possible is the total eviction of the antigen.

Allergy to nickel is one of the major aetiologies of encountered contact eczema. Nickel is present in our everyday life, and very difficult to avoid. It is found in costume and trousers buttons, jewelry, wristwatches, coins, shoe buckles, in gold plate, as well as in grey gold. Considering the difficulty of total eviction of this hapten, a product able to reduce the allergic reaction to nickel is of great interest.

According to a definition recently approved by the National Yogurt Association (NYA) or the International Life Science Institute (ILSI) in the USA, probiotics are living micro-organisms which upon ingestion in a sufficient amount, exert health benefits beyond basic nutrition. A number of studies report interactions between probiotics and the immune system, with promising results (Aso and Akazan 1992; Kaila, Isolauri et al. 1992; Gill, Rutherfurd et al. 2001). A recent study, performed with a fermented milk (containing *Lactobacillus* GG) shows curative and preventive properties due to the probiotic ingestion, and demonstrate the ability of this probiotic to lower symptoms associated with atopic eczema in the new born (Kalliomaki, Salminen et al. 2001).

DANONE has developed a fermented milk, called ACTIMEL®, using a specific symbiosis, involving 3 Lactic Acid Bacteria (*Lactobacillus casei* DN-114 001 and two traditional yogurt starters, *Lactobacillus bulgaricus* and *Streptococcus thermophilus*). ACTIMEL® is a probiotic food.

The strain DN-114 001 has been deposited at the *Collection Nationale de Cultures de Microorganismes* (CNCM, Institut Pasteur, Paris, France) under the number I-1518. This strain is designated as *Lactobacillus casei* by Danone, in a context of moving taxonomy (Dellaglio, Felis et al. 2002), and its commercial name is *Lactobacillus casei* DEFENSIS. It is designated as CNCM I-1518 in the following text.

A recent study on a model of delayed hypersensitivity type IV to dinitrofluorobenzene (DNFB) in mice shows that the daily consumption of ACTIMEL®, for at least 14 days, induces a significant and reproducible decrease (about 50%) of the intensity of the delayed hypersensitivity reaction at the contact of DNFB.

Moreover, it appears that *L. casei* CNCM I-1518 is responsible for the effect of Actimel® observed in mice (Chapat, Chemin et al. 2004). The inventors have now studied the efficiency of ACTIMEL® on a model of delayed hypersensitivity type IV to nickel in humans.

As shown in the experimental part below, in subjects allergic to nickel to whom a patch containing 5% of Nickel has been applied, a regular uptake of Actimel leads to a delayed apparition of the allergic reaction. Although the observed effect is transient, these results are relevant. Indeed, this transiency is probably due to the model that has been used, which is particularly aggressive and maximizes the delayed hypersensitivity reaction to be sure to induce a positive reaction.

Furthermore, the observed results also show that some of the symptoms of allergy to Nickel are decreased in the group of people who regularly take Actimel®.

The present invention therefore pertains to the use of the strain CNCM I-1518, for the preparation of a composition for alleviating the symptoms of a delayed-type hypersensitivity reaction and/or for delaying their appearance.

In a preferred embodiment of the invention, the composition is in the form of an aliment, for example a fermented milk composition such as a liquid yoghurt.

According to the invention, the composition can also comprise other bacterial strains, in addition to *L. casei* CNCM I-1518. For example, it can comprise *Lactobacillus bulgaricus* and/or *Streptococcus thermophilus* bacteria. Actimel®, a fermented dairy product sold by Danone™, is an example of a composition that can be used according to the invention.

In a particular embodiment of the invention, the delayed-type hypersensitivity reaction is due to an allergy to Nickel.

Importantly, the diminution of the symptoms of a delayed-type hypersensitivity reaction, when a probiotic is used according to the invention, can be either stable or transient. This diminution of symptoms of a delayed-type hypersensitivity reaction can for example include an improvement of the International Contact Dermatitis Research Group (ICDRG) score, and/or a diminution of subjective criteria, such as the itchy feeling and/or the burning feeling which follow contact with the allergen responsible for said delayed-type hypersensitivity reaction.

The figures and experimental part below will further illustrate the present invention, without limiting its scope.

FIGURE LEGENDS

Figure 2:
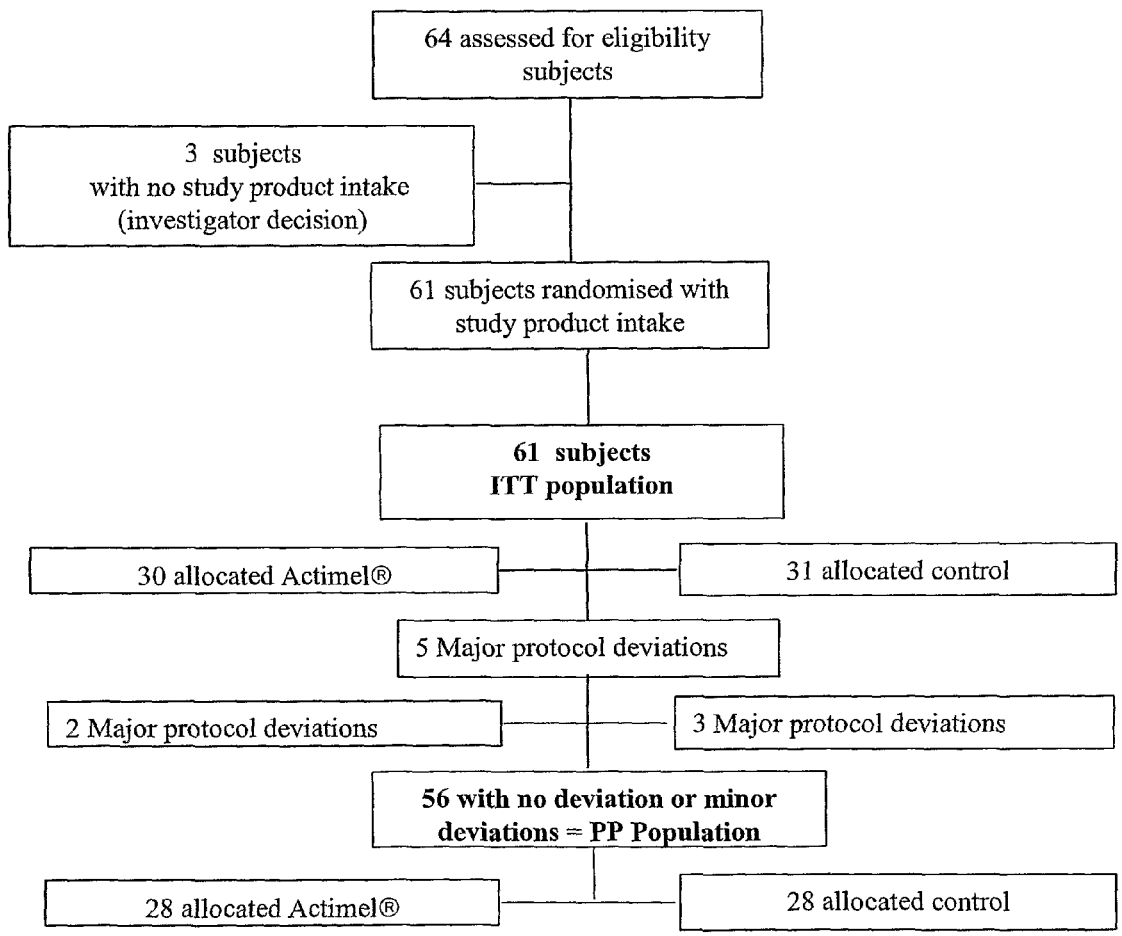
Figure 3:
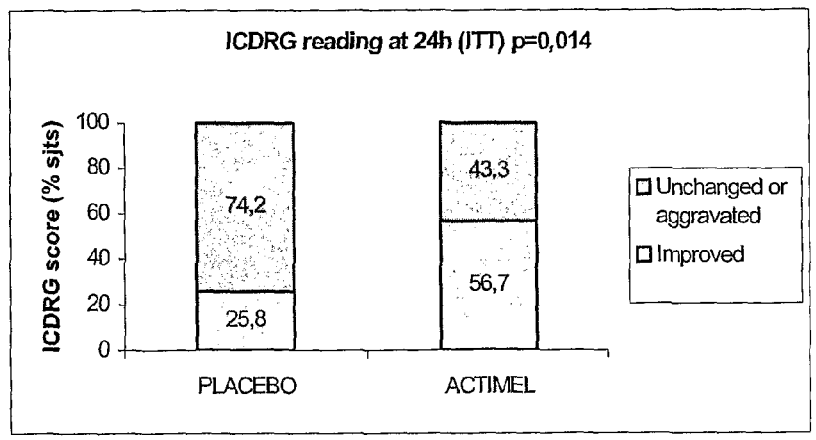
Figure 3:
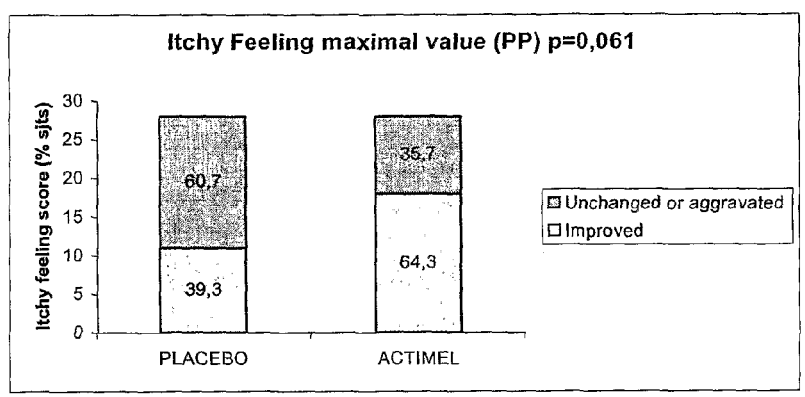
Figure 3:
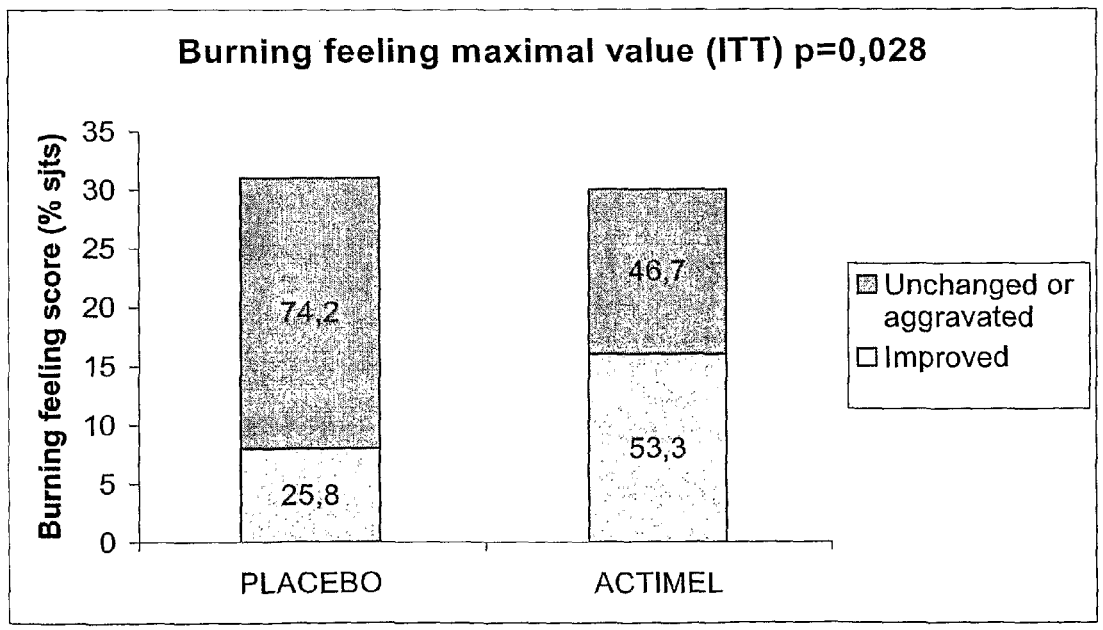

FIG. 1: study schedule
FIG. 2: disposition of the subjects
FIG. 3: Results of the study

EXAMPLES

1. Synopsis of the Study

This study concerns the evaluation of the activity of a fermented milk containing *L. casei* CNCM I-1518 in the contact allergic reaction to nickel.

Objective:

In mice, the daily consumption of ACTIMEL® for at least 14 days prior to sensitization induces a significant decrease of the intensity of the delayed hypersensitivity reaction by contact to DNFB. The aim of the present study is to double-check if ACTIMEL® has a comparable effect in humans, with a model of delayed hypersensitivity to nickel.

Methodology:

Monocentric trial, double blind, randomised, with 2 parallel groups, placebo-controlled.

Study carried over female healthy adult volunteers, allergic to nickel, aged 19 to 59 years.

Study without individual direct benefit.

Number of subjects:

64 healthy female volunteers.

Test Products:

The test products were supplied by Danone Vitapole, a Research and Development centre of Danone Group.

Name of product 1: Placebo.

Name of product 2: Actimel®.

Evaluation Criteria:

1—Effect:

Primary criteria: Diminution of the intensity of the allergic reaction estimated by a decrease in the total ICDRG score.

Secondary criteria: the secondary criteria were the other criteria of the clinical evaluation (sub-score and kinetic parameters).

2—Tolerability:

Adverse effects were recorded and the imputation to study product was evaluated.

2. Study Plan

2.1 Overall Study Design and Plan—Description

The study was carried out on 2 parallel groups: one group receiving ACTIMEL® (the "product" group) and one group receiving a placebo (the "control" group).

The study lasted 8 full weeks. The 2 first weeks were dedicated to the homogenisation and limitation of the dietary consumption of fermented dairy products (2 products per week maximum). The third week was dedicated to the application, the removal, and then the reading of the patch tests in order to produce baseline values (this period has been called "patch 1"). From week 4 to week 8, the subjects had to consume 2 bottles/day of the tested product.

An intermediate medical examination was performed during week 5 or 6. During week 8, visits were dedicated to (1) the application, (2) the removal and (3) the reading of the second patch, in order to measure the effect of the product after the period of consumption. (period named "Patch 2").

2.2 Investigation Products

This study was conducted on volunteers suffering from nickel contact allergy.

Product 1 is a placebo (acidified milk without bacteria with the same nutritional composition as Actimel).

Product 2 is Actimel®.

Actimel® is a commercial product consisting of a fermented milk containing two characteristic yoghurt bacteria (*Lactobacillus bulgaricus*, *Streptococcus thermophilus*) and a specific probiotic strain, *Lactobacillus casei* CNCM I-1518. The characteristics of Actimel® are summarized in Tables 1 and 2.

TABLE 1

| Characteristics of Actimel ® | |
| --- | --- |
| Actimel ® original | Day of finished product + 24 hours |
| Total dry matter | 18.4-19.4% |
| pH | 3.9-4.2 |
| Viscosity (mPa at 10° C.) | 10-14 |
| Density | 1,066 |

TABLE 2

| Nutritionnal composition of Actimel ® (typical value per 100 g, which corresponds to one bottle) | |
| --- | --- |
| Energy (KJ) | 350 |
| Proteins (g) | 2.8 |
| Fat (g) | 1.6 |
| Carbohydrates (g) | 14.3 |
| Calcium (mg) | 104 (theoritical value) |

Actimel® has been filled to 100 ml in neutral bottles for this study. Thanks to Danone Vitapole "know how", it has been possible to obtain a placebo close to ACTIMEL® composition (carbohydrates, lipids and proteins) and close to ACTIMEL® characteristics (acidity, texture and other organoleptics ones). It did not contain the 3 characteristic strains (*Lactobacillus casei* CNCM I-1518, *Lactobacillus bulgaricus* and *Streptococcus thermophilus*).

Both of the products belong to the dairy product family:

ACTIMEL® is manufactured in Danone factories present in several countries;

Placebo is only produced in Danone Vitapole according standard procedure of good manufactured procedure (GMP).

Subjects in the product group had to ingest a daily dosage of 2 bottles (i.e., 2×100 ml) of Actimel® during the entire duration of the product period, which is a period of 33 days.

Subjects in the control group had to ingest a daily dosage of 2 bottles (i.e., 2×100 ml) of placebo.

Subjects were assigned to the «Product» group or to the «Placebo» group according to the randomisation list.

2.3 Selection of Study Population 61 female volunteers considered as healthy, following a clinical examination, aged between 19 and 59 years were included in this study.

2.3.1 Inclusion Criteria

Person >18 y.o., female

Person allergic to nickel (scoring ++ during year 2001)

Person showing a phototype II, III, or IV skin

Person consuming regularly dairy product (at least once daily)

Person having a normal weight (body mass index comprised between 18 and 28 kg/m2 strictly)

Person having given a written informed consent for her participation to the study Person affiliated to healthcare insurance or benefiting of similar regimen

2.3.2 Exclusion Criteria

Person showing allergy for milk products

Person not enjoying the study product

Pregnant women or breastfeeding

Person not using contraceptive

Person belonging to major protected by law

Person having her back exposed (study area) to sunbath 2 weeks before enrolment

Person showing dermatological disease on the observation area (back)

Person having followed a based-on corticoids product, parenteral during the 30 days before enrolment, or local during the 15 days before enrolment Person having an acute or progressive disease Person having a personal history of metabolic or digestive pathology Person undergoing general anaesthesia within a month before inclusion Person having received an antibiotic product orally during the 2 last months before inclusion, or locally during the 15 days before inclusion.

Person receiving or having received a general or local product susceptible to interfere with the evaluation of the study parameters Person status in exclusion after participation to another clinical trial Person having received an indemnisation of more than 3800 euros for her participation to clinical trial in the 12 last months, including her participation to the present study.

Person not being registered to the national final of subjects undergoing research without individual direct benefits.

Person in a situation judged as being able to interfere with her maximal participation to the study or which could represent a particular risk for her 2.3.3 Disposition of the Subjects The disposition of the subjects is shown on FIG. 2.

2.3.4 Blinded Supply of Investigation Products

Study products were supplied in boxes provided by Danone so as to maintain the blindness for both investigators and subjects.

2.3.5 Concomitant Product

Three subjects (N°6, 10, 58) received a concomitant product included in the non inclusion criteria. These subjects were considered to be a major deviation to the protocol.

The investigator had to check the existence of intercurrent diseases (Adverse event) and concomitant product (Concomitant product) and had to record details in the subject's CRF (Case Report Form). These Adverse events and products were monitored by the sponsor.

2.3.6 Compliance

The investigator had to check the quantity of products ingested by the subjects throughout the study.

Subjects were to bring back used products (e.g., empty bottles) at each visit as well as unused products.

The quantity of products ingested was determined by the sponsor.

2.4 Evaluation Criteria 2.4.1. Appropriateness of Measurements

The study was based on measurements of both total score and sub scores of the reaction induced by 5% Ni-patch. The readings were done during 5 days at 24, 48, 72, 96 and 120 hours after the patch application.

Clinical Parameters:
total score of the reaction evaluated by physicians by using the ICDRG codification described by Wilkinson, Fregert et al. 1970 (ICDRG codification: 0: negative reaction (−), 0.5: uncertain reaction (+?), 1: weak positive reaction (+), 2: moderate positive reaction (++), 3: strong positive reaction(+++)), and
sub-scores (erythema, oedema or infiltration, vesicles, itchy feeling, burning feeling, extent of the reaction).
Kinetic parameters: progression of the reaction during time (area under curve, peak value, peak time)

2.4.2 Evaluation Variables
Primary: diminution of the intensity of the allergic reaction estimated by a decrease in the total score (ICDRG).
Secondary: all the other criteria of the clinical evaluation (sub-scores and kinetic parameters).

2.5 Data Quality Assurance—Determination of Sample Size

The calculation of the number of subjects required was based on the main criterion of product effect: clinical evaluation of the allergic reaction (qualitative response to the patch test). To detect an expected difference of 30% between the ACTIMEL® group and the placebo group, with a power of 70% and an α level of 5% (considering an improvement of 35% in the ACTIMEL® group and of 5% in the placebo group), the number of subjects to be included in each group was 28.

3. Product Effect Evaluation 3.1 Analyses of the primary criterion 3.1.1 Results concerning the main criterion of efficacy at 24 h The evolution of the ICDRG total score was compared between the two groups at the three first readings. Results are displayed in table 3 for the ITT population and table 4 for the PP population.

The evolution showed an improvement at the first reading favourable to Actimel®: 56.7% of the ITT population was improved in the Actimel® group versus 25.8% for the placebo. As shown on FIG. 3, the difference was statistically significant (chi$^2$ p-value=0.014). However, no significant difference appeared at the other readings.

The results with the PP population were consistent and showed a significant difference (chi$^2$ p-value=0.031) at the first reading favourable to Actimel®: 57.1% of the subjects were improved versus 28.6% in the placebo group. There was no difference on the PP population for the two other readings.

TABLE 3

Total score ICDRG, reading 1 - evolution (ITT)

| Total score | PLACEBO | ACTIMEL ® | ITT |
|---|---|---|---|
| Improved | 8 (25.8%) | 17 (56.7%) | 25 (41.0%) |
| Unchanged or aggravated | 23 (74.2%) | 13 (43.3%) | 36 (59.0%) |
| Total | 31 (100.0%) | 30 (100.0%) | 61 (100.0%) |

P-value for Chi-Square = 0.014

TABLE 4

Total score ICDRG, reading 1 - evolution (PP)

| Total score | PLACEBO | ACTIMEL ® | PP |
|---|---|---|---|
| Improved | 8 (28.6%) | 16 (57.1%) | 24 (42.9%) |
| Unchanged or aggravated | 20 (71.4%) | 12 (42.9%) | 32 (57.1%) |
| Total | 28 (100.0%) | 28 (100.0%) | 56 (100.0%) |

P-value for Chi-Square = 0.031

3.1.2 Analyses of Primary Criterion on the 5 Readings (ITT and PP Populations)

3.1.2.1 ITT Population

The primary criterion of study product effect was based on the ICDRG total score. Allergy to nickel was defined by a score $\geq$++ (moderate positive or strong positive). The maximal total score was defined as the maximal score observed among the 5 readings of each patch. The difference between patch 1 and patch 2 determined whether the subject was improved, unchanged or aggravated.

In the ITT population, 30% of the subjects receiving Actimel® were improved at patch 2 versus 25.8% in the placebo group. Despite a discrete advantage among the 5 readings, there was no statistical difference between the two groups for the ICDRG maximal total score (see also table 6 and FIG. 3). No significant difference or trend appears in the measurement and comparison of the area under the curve (AUC) at patch 2 or in evolution (comparison with patch 1) (Table 5).

TABLE 5

Total Score "ICDRG": Area Under the Curve (AUC)

Placebo population

| ICDRG | N | Mean/Median | SD/SEM* | mini-maxi | Q1-Q3 |
|---|---|---|---|---|---|
| Patch 2 AUC | 31 | 6.8/7.3 | 3.3/0.6 | 0.0-12.0 | 3.9-9.5 |
| AUC evolution | 31 | −1.3/−1.0 | 2.3/0.4 | −7.5-1.5 | −3.1-0.8 |

ACTIMEL ® population

| | N | Mean/Median | SD/SEM | mini-maxi | Q1-Q3 |
|---|---|---|---|---|---|
| Patch 2 AUC | 30 | 7.0/7.4 | 2.5/0.5 | 1.5-11.6 | 5.5-8.6 |
| AUC evolution | 30 | −0.9/−1.1 | 1.9/0.3 | −4.4-4.2 | −2.0-0. |

| | Student |
|---|---|
| Patch 2 AUC | 0.714 |
| AUC evolution | 0.508 |

*SD/SEM = Standard Deviation/Standard Error Mean

TABLE 6

Total score "ICDRG"; maximal value

| ICDRG | PLACEBO | ACTIMEL ® | ITT |
|---|---|---|---|
| Improved | 8 (25.8%) | 9 (30.0%) | 17 (27.9%) |
| Unchanged or aggravated | 23 (74.2%) | 21 (70.0%) | 44 (72.1%) |
| Total | 31 (100.0%) | 30 (100.0%) | 61 (100.0%) |

P-value for chi-square = 0.715

3.1.2.2 PP population

No statistically significant difference was observed between the placebo and the study product groups when comparing the results obtained at patch 2. In particular, the same number of subjects of each group showed an improved reaction at patch 2 (when compared with their reaction at patch 1).

3.2 Analysis of Secondary Criteria

The secondary criteria analysis was performed using the sub-score for the different elements constitutive of an allergic reaction at a clinical level.

3.2.1 Secondary Criterion: Itchy Feeling
3.2.1.1 ITT Population

There was a trend (chi$^2$ p=0.096) for ACTIMEL® effect on the "itchy feeling" at the maximal value (60.0% subjects improved in the ACTIMEL® group versus 38.7% in the placebo group). See table 7.

TABLE 7

Sub-score: "Itchy feeling" (ITT); maximal value

| Itchy feeling | PLACEBO | ACTIMEL ® | ITT |
|---|---|---|---|
| Improved | 12 (38.7%) | 18 (60.0%) | 30 (49.2%) |
| Unchanged or aggravated | 19 (61.3%) | 12 (40.0%) | 31 (50.8%) |
| Total | 31 (100.0%) | 30 (100.0%) | 61 (100.0%) |

P-value for Chi-Square = 0.096

3.2.1.2 PP Population

As shown in table 8, there was also a trend (chi$^2$ p=0.061) for ACTIMEL® on the study product effect criterion (64.3% subjects improved in the ACTIMEL® group versus 39.3% in placebo group). Hence, ACTIMEL® appears to reduce the "itchy feeling" both in ITT and PP populations (see FIG. 3)

TABLE 8

Sub-score: "Itchy feeling"(PP); maximal value

| Itchy feeling | PLACEBO | ACTIMEL ® | ALL |
|---|---|---|---|
| Improved | 11 (39.3%) | 18 (64.3%) | 29 (51.8%) |
| Unchanged or aggravated | 17 (60.7%) | 10 (35.7%) | 27 (48.2%) |
| Total | 28 (100.0%) | 28 (100.0%) | 56 (100.0%) |

P-value for Chi-square: 0.061

3.2.2 Secondary Criterion: Burning Feeling
3.2.2.1 ITT Population

There was a significant difference (chi$^2$ p=0.028) for ACTIMEL® on the study product effect criterion (53.3% subjects improved in the ACTIMEL® group versus 25.8% in the placebo group). See table 9 and FIG. 3.

TABLE 9

Sub-score: "Burning feeling" (ITT); maximal value

| Burning feeling | PLACEBO | ACTIMEL ® | ITT |
|---|---|---|---|
| Improved | 8 (25.8%) | 16 (53.3%) | 24 (39.3%) |
| Unchanged or aggravated | 23 (74.2%) | 14 (46.7%) | 37 (60.7%) |
| Total | 31 (100.0%) | 30 (100.0%) | 61 (100.0%) |

P-value for Chi-Square = 0.028

3.2.2.2 PP Population

There was a significant difference (chi$^2$ p=0.014) for Actimel® on the study product effect criterion (57.1% subjects improved in Actimel® group versus 25.0% in placebo group). The results are shown in table 10.

TABLE 10

Sub-score: "Burning feeling"; maximal value (PP)

| Burning feeling | PLACEBO | ACTIMEL ® | ALL |
|---|---|---|---|
| Improved | 7 (25.0%) | 16 (57.1%) | 23 (41.1%) |
| Unchanged or aggravated | 21 (75.0%) | 12 (42.9%) | 33 (58.9%) |
| Total | 28 (100.0%) | 28 (100.0%) | 56 (100.0%) |

P-value for Chi-square: 0.014

4. Conclusion on Effect of the Study Product

The evolution of the primary criterion showed an improvement at the first reading favourable to Actimel®: 56.7% of the ITT population was improved in the Actimel® group versus 25.8% for the placebo. The difference was statistically significant (chi$^2$ p-value=0.014). In addition, a significant effect was also shown on the PP population (chi$^2$ p-value=0.031) at the first reading.

However, no difference was shown on the main criteria (total score ICDRG) at maximal value for the study product effect either in ITT or PP population.

Upon the secondary criteria "itchy feeling", a significant trend favourable to Actimel® was shown for the PP population: 64.3% subjects improved in the Actimel® group versus 39.3% in placebo group (chi$^2$ p-value=0.061). This trend was also found on the ITT population (chi$^2$=0.096).

Upon the secondary criteria "burning feeling" on the ITT population, there was a significant difference (chi$^2$ p=0.028) for Actimel® on the study product effect criterion (53.3% subjects improved in the Actimel® group versus 25.8% in the placebo group). This statistically significant difference was also found on the PP population (chi$^2$ p=0.014).

The above results globally showed an early and transient product effect: 24 h after applying the Ni allergen to allergic subjects, the delayed hypersensitivity reaction to Nickel that was observed was far less intense in subjects taking Actimel® than in control subjects. Furthermore, when this allergic reaction was set up, the functional symptoms such as itchy feeling and burning feeling remained limited.

The model used in this study is a patch test, in which a patch comprising 5% Ni is applied onto the skin of allergic volunteers. This test maximizes the delayed hypersensitivity reaction, and has been used because it enables reproducible clinical responses. The transiency of the observed effect of Actimel® is most probably due to the maximizing character of the test that has been used: the intensity of the immune reaction hides the probiotic effect, which can still be observed on the functional symptoms.

This kind of discrepancy between objective and subjective criteria has already been observed in other studies involving inflammatory reactions:

In a recent study to evaluate the clinical and anti-inflammatory effect of probiotic supplementation in children with atopic dermatitis (AD), Rosenfeldt et al conducted a double-blind, placebo-controlled, crossover trial, in which 2 probiotic *Lactobacillus* strains were given in combination for 6 weeks to 1- to 13-years old children with atopic dermatitis (AD). The patients' evaluations were registered after each intervention (i.e., better, unchanged, or worse). The clinical severity of the eczema was evaluated by using the scoring atopic dermatitis (SCORAD) score. The authors have shown that after active treatment, 56% of the patients experienced improvement of the eczema, whereas only 15% believed their symptoms had improved after placebo (P=0.001). The total SCORAD index, however, did not change significantly (Rosenfeldt and Benfeldt et al. 2003).

In case of urticaria, the uptake of antihistaminics can improve the itchy feeling without necessarily provoking disappearance of the wheal. The effect of Actimel® can be compared to the effect of antihistaminics in urticaria.

REFERENCES

Aso, Y. and H. Akazan (1992). "Prophylactic effect of a *Lactobacillus casei* preparation on the recurrence of superficial bladder cancer. BLP Study Group." *Urol Int* 49(3): 125-9.

Chapat, L., K. Chemin, et al. (2004). P "*Lactobacillus casei* reduces CD8(+) T cell-mediated skin inflammation." *Eur J Immunol* 34(9): 2520-8.

Dellaglio, F., G. E. Felis, et al. (2002). "The status of the species *Lactobacillus casei* (Orla-Jensen 1916) Hansen and Lessel 1971 and *Lactobacillus paracasei* Collins et al. 1989. Request for an opinion." *Int J Syst Evol Microbiol* 52(Pt 1): 285-7.

Gill, H. S., K. J. Rutherfurd, et al. (2001). "Enhancement of immunity in the elderly by dietary supplementation with the probiotic *Bifidobacterium lactis* HN019." *Am J Clin Nutr* 74(6): 833-9.

Kaila, M., E. Isolauri, et al. (1992). "Enhancement of the circulating antibody secreting cell response in human diarrhea by a human *Lactobacillus* strain." *Pediatr Res* 32(2): 141-4.

Kalliomaki, M., S. Salminen, et al. (2001). "Probiotics in primary prevention of atopic disease: a randomised placebo-controlled trial." *Lancet* 357(9262): 1076-9.

Krasteva, M., J. Kehren, et al. (1999)a. "Contact dermatitis I. Pathophysiology of contact sensitivity." *Eur J Dermatol* 9(1): 65-77.

Krasteva, M., J. Kehren et al. (1999)b. "Contact dermatitis II. Clinical aspects and diagnosis." *Eur J Dermatol* 9(2): 144-59.

Rosenfeldt, V., E. Benfeldt, et al. (2003). "Effect of probiotic Lactobacillus strains in children with atopic dermatitis." *J Allergy Clin Immunol* 111(2): 389-95.

Wilkinson, D. S., S. Fregert, et al. (1970). "Terminology of contact dermatitis." *Acta Derm Venereol* 50(4): 287-92.

The invention claimed is:

1. A method of alleviating the symptoms of delayed-type hypersensitivity reaction and/or of delaying the appearance of said symptoms comprising administering a composition comprising *Lactobacillus casei* CNCM I-1518 to a human subject in need thereof, wherein said delayed-type hypersensitivity reaction is an allergy to nickel allergen.

2. The method of claim 1, wherein said composition is in the form of an aliment.

3. The method of claim 1, wherein said composition is a fermented milk composition.

4. The method of claim 1, wherein said composition also comprises *Lactobacillus bulgaricus* and/or *Streptococcus thermophilus* bacteria.

5. The method of claim 1, wherein the alleviating of the symptoms of the delayed-type hypersensitivity reaction includes an improvement of the International Contact Dermatitis Research Group (ICDRG) score.

6. The method of claim 1, wherein the alleviating of the symptoms of the delayed-type hypersensitivity reaction includes alleviating the itchy feeling which follows contact with the nickel allergen responsible for said delayed-type hypersensitivity reaction.

7. The method of claim 1, wherein the alleviating of the symptoms of the delayed-type hypersensitivity reaction includes alleviating the burning feeling which follows contact with the nickel allergen responsible for said delayed-type hypersensitivity reaction.

* * * * *